United States Patent [19]

Wallach et al.

[11] Patent Number: 4,952,550

[45] Date of Patent: Aug. 28, 1990

[54] PARTICULATE ABSORBENT MATERIAL

[75] Inventors: Donald F. H. Wallach, Hollis; An-Cheng Chang, Nashua, both of N.H.

[73] Assignee: Micro Vesicular Systems, Inc., Nashua, N.H.

[21] Appl. No.: 490,356

[22] Filed: Mar. 8, 1990

Related U.S. Application Data

[63] Continuation-in-part of Ser. No. 320,944, Mar. 9, 1989.

[51] Int. Cl.$^5$ .................... B01J 13/00; B01J 20/22; B01J 20/26
[52] U.S. Cl. .................... 502/404; 252/194; 252/315.3; 604/368
[58] Field of Search ............. 502/404; 252/194, 315.3; 604/368

[56] References Cited

U.S. PATENT DOCUMENTS

| | | | |
|---|---|---|---|
| 3,969,280 | 7/1976 | Sayce et al. | 252/522 |
| 4,090,013 | 5/1978 | Ganslaw et al. | 526/15 |
| 4,160,063 | 7/1979 | Titus | 428/389 |
| 4,454,055 | 6/1984 | Richman et al. | 252/194 |
| 4,486,355 | 12/1984 | Majewicz | 252/315.3 |
| 4,548,847 | 10/1985 | Aberson et al. | 252/194 X |
| 4,610,678 | 9/1986 | Weisman et al. | 604/368 |
| 4,786,415 | 11/1988 | Shibata et al. | 502/404 X |
| 4,812,486 | 3/1989 | Hosokawa et al. | 502/404 X |
| 4,826,880 | 5/1989 | Lesniak et al. | 521/53 |

FOREIGN PATENT DOCUMENTS 1152483  8/1983  Canada ........................ 502/404

Primary Examiner—Patrick P. Garvin
Attorney, Agent, or Firm—Lahive & Cockfield

[57] ABSTRACT

The present invention features methods of making absorbent material which exhibit excellent absorption for saline and other liquids as well as being biodegradable. The methods of the invention form a particulate which can be stored in dry form and rehydrated at any time. The particulate can be used to replace the presently utilized polyacrylate superabsorbers. The base material used in the methods of the invention is a carboxylated cellulosic material such as carboxymethylcellulose, preferably, a carboxymethylcellulose having a DS, or Degree of Substitution, of 0.5 or greater. The carboxylated cellulose material is reacted with two distinct agents; a cross-linking agent and a hydrophobicity agent to make the final absorbent.

20 Claims, No Drawings

PARTICULATE ABSORBENT MATERIAL

REFERENCE TO RELATED APPLICATIONS

The present application is a continuation-in-part of U.S. Pat. Application Ser. No. 320,944, entitled "Biodegradable Superabsorbing Sponge," filed Mar. 9, 1989, the disclosure of which is incorporated herein by reference. The application is also related to U.S. Pat. Application Ser. No. 371,210, entitled "Biodegradable Incontinence Device," filed June 26, 1989.

BACKGROUND OF THE INVENTION

The present invention relates to absorbent particles which swell in the presence of aqueous solutions including saline and urine to many times their own weight. These absorbent materials are biodegradable and have absorptive properties equal to or higher than those of present superabsorbers.

Biodegradability of disposable products is no longer a preferred option; it has become a necessity. As the number of disposables in society has grown, the land fills and others methods of treatment for these disposables have been strained to the limits. Plastics are just one form of the problem of disposables while absorbent materials such as polyacrylates which are commonly used, e.g., in disposable diapers, have degradation times in the thousands of years. While the superabsorber such as the polyacrylates have advantages because of their high absorptive capabilities so that less is needed to attract a large amount of liquid, the non-biodegradability of these products makes them unacceptable if alternatives can be achieved.

Particulate superabsorbers can be used either in lose or packed form or else can be dispersed among fibers, e.g., cellulose fluff, to act as part of a liquid absorption system. However, if they are used in a packed form, the gel blocking problem must be ameliorated in order to provide optimum action.

Accordingly, an object of the invention is to provide a biodegradable superabsorbent particle which is competitive with the polyacrylate superabsorbers in terms of uptake for aqueous solutions and saline.

Another object of the invention is to provide methods of making biodegradable superabsorbers which use inexpensive material and are rapid.

A further objection of the invention is to provide a superabsorber which can act as a delivery system for a variety of materials, e.g., enzymes.

These and other objects and features of the invention will be apparent from the following description.

SUMMARY OF THE INVENTION

The present invention features methods of making absorbent material which exhibit excellent absorption for saline and other liquids as well as being biodegradable. The methods of the invention form a particulate which can be stored in dry form and rehydrated at any time. The particulate can be used to replace the presently utilized polyacrylate superabsorbers.

The absorptive material made using the methods of the invention differs from acrylate absorbents in that it is biodegradable; and it is hydrophobic which assists in limiting gel blocking and reduces clumping. The hydrophobic aspect of the present particulates makes them distinct from earlier superabsorbers.

The base material used in the methods of the invention is a carboxylated cellulosic material such as carboxymethylcellulose. However, any cellulose derivative which has substantial carboxylation can be used. The preferred carboxylated cellulose is a carboxymethylcellulose having a DS, or Degree of Substitution, of 0.5 or greater, most preferably greater than 0.7. Carboxymethylcellulose with this high Degree of Substitution can have such a large amount of cross-linking that it would form an unworkable, almost glue-like material without the hydrophobicity treatment of the present invention.

The carboxylated cellulose material is reacted with two distinct agents; a cross-linking agent and a hydrophobicity agent. The order of reaction can change the properties of the final absorbent, with the reaction first with the cross-linking agent yielding more of a shell-like absorber and, consequently, a firmer particle, while their reaction with the hydrophobicity agent first will yield a particle having higher overall absorptive capabilities with absorption throughout the body of the particle. The preferred cross-linking agents are those which are metal containing and include a metal with an effective valence of at least three such as aluminum, chromium, or iron. The most preferred cross-linking agents are acetates, alkoxides such as ispropoxides and hydroxides, and chlorides. These include materials such as aluminum acetate, aluminum isopropoxide, aluminum hydroxide, ferric chloride, and mixtures thereof.

Hydrophobicity agents useful in the methods of the invention include monobasic and polybasic carboxylic acids or their salts, chlorides or anhydrides, most preferably those with 2–16 carbon atoms. Examples of useful hydrophobicity agents include acetic acid, proprionic acid, butyric acid, isobutyric acid, acetyl chloride, sodium acetate, sodium proprionate, proprionyl chloride, sodium butyrate, acetic anhydride, proprionyl anhydride, succinic acid, adipic acid, phthalic acid, citric acid, and mixtures thereof.

The reactions between the carboxylated cellulosic material and the cross-linking and/or hydrophobicity agent can be carried out in either aqueous or organic solutions. If an aqueous solvent is used, a moderate concentration saline, e.g., 0.9%, is preferred to get a better charge separation in the interior of the particle while organic solvent such as neutral petroleum spirits may be use if the reactants chosen are not readily soluble in aqueous solutions. In one most preferred embodiment to the invention, carboxymethylcellulose is first pre-swollen in an aqueous solution which allows better access of the cross-linking and hydrophobicity agents to the interior of the particle. In addition, pre-treatment of the carboxymethylcellulose with a small quantity of an alcohol such as isopropyl alcohol may improve wetting and, accordingly, the reactions.

The following description will further explain the methods of the invention.

DESCRIPTION OF THE INVENTION

The preferred absorbers of the present invention use a carboxymethylcellulose having a DS of 0.7 or above in order to provide sufficient cross-linking while allowing the hydrophobicity agent to eliminate the glue-like clumping problem. Although it is not necessary for understanding the invention, it is theorized that the metal ion, e.g., aluminum, reacts with the carboxyl groups on the adjacent chains of carboxymethylcellulose, forming an ionic cross-link between the chains. The aluminum has a third group thereon, most normally a hydroxide group although it could be an isopropyl or acetate group. The hydrophobic group, which most preferably is a small group such as acetate or proprionate is linked to a carboxymethylcellulose residue by aluminum ions as already described for cross-linking. The reason that the shorter chain carboxylic acids are preferred, e.g., acetate or proprionate is that with the same Degree of Substitution using larger molecules such as benxoic or palmitic acid, the hydrophobicity is so great that the water is not as easily accessible to the interior of the molecule. To use the longer chain molecules the degree of hydrophobic substitution must be much lower.

The reason why the particulates of the present invention work so well as superabsorbers is not completely understood but is theorized that the Donnan effect may be involved. The Donnan effect relates to a charge separation whereby having a high concentration of net negative charge in the interior of the particle will cause flow of saline. This type of effect is expected since the absorption for the particulates made using the present methods is improved for saline as compared with a salt free aqueous solution.

The following Examples will further illustrate the methods of the invention.

EXAMPLE 1

In this Example, an organic method of making the particulate is described. In this, and all the following Examples, similar carboxymethylcellulose (CMC) was used. The carboxymethylcellulose had a DS of about 0.7 and was first sieved to remove any particles smaller than 500 microns. The particular CMC used was CMC 7H obtained from Aqualon.

Five g of CMC was dissolved in 4 ml of petroleum ether having a boiling point of 70–90° C. The petroleum ether contained 1 g of aluminum isopropoxide (Manalox 130, Manchem, Princeton, N.J.). The resulting slurry was stirred at 45–55° C. in a closed vessel. After 2–4 hours (determined by no further release of isoproponal), 0.4–0.8 g of anhydrous glacial acetic acid is added and stirring is continued for another 1–2 hours. After completion of the reaction, the solvent is removed from the slurry by filtration, the slurry is washed with other solvents such as petroleum ether and/or anhydride isopropl alcohol and air dried.

The resulting product was tested by uptake in capillary action with 0.15 N NaCl under applied load of 0.22 lbs./in$^2$ for sixty minutes at room temperature. The amount of fluid uptake was then measured gravimetrically. The superabsorber absorbed 15 ml saline/g superabsorber.

EXAMPLE 2

In this Example, the same carboxymethylcellulose was formed into a particle using an aqueous procedure. First, approximately 1 g of the CMC was pre-wet with 0.4 g of an alcohol such as isopropyl alcohol. The alcohol was removed and then 10 g of saline containing aluminum acetate (20 mg/g CMC) and 40 mg glacial acetic acid was added. The reaction was allowed to proceed for 4 hours at 50° C. The swollen particles were then removed and dried under a hot air flow.

Using the same test of described in Example 1, the saline uptake under load was approximately 18 ml/g of superabsorber.

EXAMPLE 3

In the Example, the carboxymethylcellulose was first allowed to swell for several hours in normal saline (0.9%) before the reactions described in Example 2 were carried out. By allowing the particles to swell to five times their initial weight before reaction, a value of approximately 17 ml/g was obtained using the weight test. By allowing the particles to swell to approximately ten times their initial volume, a value of 19 ml/g was obtained. The pre-swelled described herein was "free" swelling, e.g., swelling without any applied load.

There are several factors which can be modified in order to obtain optimum performance for a particular task. First, a more highly cross-linked absorber will exhibit a slower rate of saline uptake that will be able to hold more total saline. Further, if the reaction between the hydrophobic agent and the carboxylated cellulosic material is carried out before the cross-linking, a more absorbent material is formed. In any case, not all of the carboxyl groups were involved in the cross-linking. The highly cross-linked materials have 15–20 mole percent cross-linked while in some materials, such as that described in Example 2, only about 1 mole percent cross-linking is used.

EXAMPLE 4

In this Example, a low molecular weight carboxymethylcellulose (CMC) was used as a basis of the particulate superabsorber. Two distinct hydrophobicity agents, a monobasic acid and a bibasic acid, were used to modulate the cross-linking so as to obtain a product having improved properties. Without the use of both hydrophobicity agents, the material becomes too heavily cross-linked to use.

One gram of low molecular weight CMC (Akzo PL820) was mixed with 0.5 g of isopropanol. Thirty grams of a cross-linking/hydrophobicity agent solution was then added. This solution was made with 90 mg NaCl, 20 mg aluminum acetate/borate, 40 mg glacial acetic acid, and 50 mg succinic acid in 28 ml water. The resulting solution is stirred continuously until a homogeneous gel is formed. The gel is then transferred into a syringe and injected into 150 g of an isopropyl alcohol solution through a 16 gauge needle. A white precipitate in the form of small fibers appears in the alcohol solution. The alcohol is removed by filtration and evaporation and the resulting fibers are air dried.

Using the same test as described in Example 1, the material showed an absorption of 15 ml saline/g superabsorber under load. The particulate superabsorber also showed a free-swell (swelling without any applied load) of 48 ml saline/g superabsorber.

A further test was conducted with this material by placing the free-swollen superabsorber in a "tea-bag" of a non-woven fabric with a 150 mm mesh. The tea-bags were transferred to 50 ml centrifuge tubes and centrifuged to 3000 X g for 30 minutes. At the end of 30 minutes centrifugation, the free fluid was collected. The amount of liquid released was determined gravimetrically. The results show a liquid retention after centrifugation of approximately 22 ml saline/g superabsorber.

In addition to those described above, other means of making a particulate could be used. For example, a gel could be formed which is then dehydrated and ground to particulate form. Although this procedure can be useful, see Example 1 of the previously cited U.S. Pat. Application Ser. No. 320,944, is unlikely to yield particles of a single size without significant waste of material. Further, tests of particulate made using the grinding procedure without adding additional cellulose (such as described in the aforementioned Example) yielded an absorption under load of 10–18 ml/mg. The values using the methods described herein are much more consistent and simpler without yielding problems of gel blocking.

Those skilled in the art will be able to determine other modifications of the Example procedures and materials set forth herein. Such other modifications are within the scope of the following claims.

What is claimed is:

1. A method of making a particulate absorbent material comprising the steps of:
   A. reacting a carboxylated cellulosic material with
      i. a cross-linking agent, and
      ii. a hydrophobicity agent;
   B. separating the reaction product; and
   C. removing water from said reaction product until it is substantially dehydrated and a particulate is formed of said absorbent material.

2. The method of claim 1 wherein said carboxylated cellulosic compound is selected from the group consisting of carboxymethylcellulose with DS valves of 0.5 or greater.

3. The method of claim 2 wherein said carboxymethylcellulose reacts with said cross-linking agent before the reaction of said carboxymethylcellulose with said hydrophobicity agent.

4. The method of claim 2 wherein said carboxymethylcellulose reacts with said hydrophobicity agent before the reaction of said carboxymethylcellulose with said cross-linking agent.

5. The method of claim 2 wherein said cross-linking agent is selected from the group consisting of cross-linking agents which include a metal having an effective valence of at least 3.

6. The method of claim 5 wherein said metal ion is selected from the group consisting of aluminum ions, chromium ions, and iron ions.

7. The method of claim 6 wherein said cross-linking agents are selected from the group consisting of aluminum acetate, aluminum isopropoxide, aluminum hydroxide, ferric chloride, and mixtures thereof.

8. The method of claim 2 wherein said hydrophobicity agent is selected from the group consisting of monobasic and polybasic carboxylic acids and salts, chlorides, and anhydrides thereof.

9. The method of claim 8 wherein said carboxylic acid is selected from the group consisting of monobasic and polybasic carboxylic acids having 2–16 carbon atoms, and salts, chlorides, and anhydrides thereof.

10. The method of claim 9 wherein said carboxylic acid agent is selected from the group consisting of acetic acid, proprionic acid, butyric acid, isobutyric acid, acetic chloride, sodium acetate, sodium propionate, proprionyl chloride, sodium butyrate, acetic anhydride, proprionyl anhydride, succinic acid, adipic acid, phthalic acid, citric acid, and mixtures thereof.

11. The method of claim 2 wherein said reactions of said carboxymethylcellulose with said cross-linking agent and said carboxymethylcellulose with said hydrophobicity agent are carried out in an organic solvent.

12. The method of claim 2 wherein said reactions of said carboxymethylcellulose with said cross-linking agent and said carboxymethylcellulose with said hydrophobicity agent are carried out in an aqueous solvent.

13. The method of claim 12 wherein said carboxymethylcellulose is pre-swollen in an aqueous solution before reaction with said cross-linking agent and said hydrophobicity agent.

14. A method of making a particulate absorbent comprising the steps of:
   forming an emulsion of carboxymethylcellulose having a DS greater than 0.5 in an organic solvent;
   reacting said carboxymethylcellulose with a cross-linking agent selected from the group consisting of primary and secondary chromium and aluminum alkoxides, ferric chloride, aluminum and chromium hydroxides, aluminum and chromium acetates, and mixtures thereof;
   reacting the carboxymethylcellulose with a hydrophobicity agent selected from the group consisting of monobasic and polybasic carboxylic acids having 2–16 carbon atoms, and salts, chlorides, and anhydrides thereof; and
   removing said organic solvent.

15. The method of claim 14 wherein said reaction with said hydrophobicity agent takes place before the reaction with said cross-linking agent.

16. The method of claim 14 wherein said reaction with said cross-linking agent takes place before the reaction with said hydrophobicity agent.

17. A method of making a particulate absorbent comprising the steps of:
   swelling particulates of carboxymethylcellulose having a DS greater than 0.5 in an aqueous solvent;
   reacting said carboxymethylcellulose with a cross-linking agent selected from the group consisting of primary and secondary chromium and aluminum alkoxides, ferric chloride, aluminum and chromium hydrates, aluminum and chromium acetates, and mixtures thereof;
   reacting the carboxymethylcellulose with a hydrophobicity agent selected from the group consisting of monobasic and polybasic carboxylic acids havings 2–16 carbon atoms, and salts, chlorides, and anhydrides thereof; and
   removing said aqueous solvent.

18. The method of claim 17 wherein said reaction with said hydrophobicity agent is carried out before said reaction with said cross-linking agent.

19. The method of claim 17 wherein said reaction with said cross-linking agent is carried out before said reaction with said hydrophobicity agent.

20. The method of claim 17 wherein said carboxymethylcellulose is reacted with an alcohol before the reaction with said cross-linking agent and the reaction with said hydrophobicity agent.

* * * * *